(12) United States Patent
Mohr Durdez

(10) Patent No.: US 12,251,229 B2
(45) Date of Patent: Mar. 18, 2025

(54) COMPUTING DEVICE FOR DETECTING HEART RHYTHM DISORDERS

(71) Applicant: SUBSTRATE HD, Marseilles (FR)

(72) Inventor: Théophile Mohr Durdez, Marseilles (FR)

(73) Assignee: SUBSTRATE HD, Marseilles (FR)

( * ) Notice: Subject to any disclaimer, the term of this patent is extended or adjusted under 35 U.S.C. 154(b) by 1173 days.

(21) Appl. No.: 17/044,126

(22) PCT Filed: Mar. 26, 2019

(86) PCT No.: PCT/FR2019/050682
§ 371 (c)(1),
(2) Date: Sep. 30, 2020

(87) PCT Pub. No.: WO2019/186050
PCT Pub. Date: Oct. 3, 2019

(65) Prior Publication Data
US 2021/0121118 A1    Apr. 29, 2021

(30) Foreign Application Priority Data

Mar. 30, 2018  (FR) ...................................... 1852850

(51) Int. Cl.
*A61B 5/361*    (2021.01)
*A61B 5/00*     (2006.01)
(Continued)

(52) U.S. Cl.
CPC ............ *A61B 5/361* (2021.01); *A61B 5/7267* (2013.01); *A61B 5/746* (2013.01);
(Continued)

(58) Field of Classification Search
CPC ....... A61B 5/361; A61B 5/7267; A61B 5/746; A61B 5/287; A61B 5/6852;
(Continued)

(56) References Cited

U.S. PATENT DOCUMENTS 6,714,925 B1 *  3/2004  Barnhill ................ G06F 18/211
                                                      706/48
7,225,013 B2 *  5/2007  Geva .................... A61B 5/7275
                                                      600/513
(Continued)

FOREIGN PATENT DOCUMENTS

CN    103961086 A    8/2014
CN    105228508 A    1/2016

OTHER PUBLICATIONS

Narayan, S. M., et al. "Evaluating Fluctuations in Human Artrial Fibrillatory Cycle Legnth UsingMonophasic Action Potentials" 29(11): 1209-1218 (Nov. 2006) cited in ISR submitted herewith.
(Continued)

*Primary Examiner* — Carl H Layno
*Assistant Examiner* — Manolis Pahakis
(74) *Attorney, Agent, or Firm* — Troutman Pepper Locke LLP

(57) ABSTRACT

A device for detecting heart rhythm disorders comprises a memory designed to receive cardiac electrogram data and to store data defining a first classification model for detecting heart rhythm disorders and a second classification model for detecting heart rhythm disorders, a classifier designed to analyze cardiac electrogram data based on a classification model, and to return a classification value, and a driver designed to store cardiac electrogram data in the memory and analyze the data with the classifier, and to return alert data when the analysis by the classifier returns a classification value associated with a heart rhythm disorder.

6 Claims, 1 Drawing Sheet

(51) Int. Cl.
*G06F 18/21* (2023.01)
*G06N 20/00* (2019.01)
*G16H 50/20* (2018.01)

(52) U.S. Cl.
CPC ......... *G06F 18/2185* (2023.01); *G06N 20/00* (2019.01); *G16H 50/20* (2018.01)

(58) Field of Classification Search
CPC ... A61B 2505/05; A61B 5/046; A61B 5/0422; G16H 50/20; G16H 50/30; G16H 50/70
See application file for complete search history.

(56) References Cited

U.S. PATENT DOCUMENTS

| | | | | |
|---|---|---|---|---|
| 8,452,387 | B2* | 5/2013 | Osorio | A61B 5/316 600/509 |
| 8,827,912 | B2* | 9/2014 | Bukhman | A61B 5/349 600/509 |
| 8,858,448 | B2* | 10/2014 | Thakur | A61B 5/1107 600/481 |
| 8,965,490 | B2* | 2/2015 | Lee | A61B 5/061 600/509 |
| 9,020,583 | B2* | 4/2015 | Zhang | A61B 5/366 600/517 |
| 9,119,551 | B2* | 9/2015 | Qi | A61B 8/0841 |
| 9,675,286 | B2* | 6/2017 | Diab | A61B 5/14551 |
| 10,811,141 | B2* | 10/2020 | Hu | G16H 10/60 |
| 2004/0193064 | A1* | 9/2004 | Shusterman | A61B 5/357 600/504 |
| 2007/0293894 | A1 | 12/2007 | Zhang et al. | |
| 2008/0109041 | A1* | 5/2008 | de Voir | A61N 1/37 607/7 |
| 2008/0208072 | A1* | 8/2008 | Fadem | A61B 5/291 600/544 |
| 2010/0249626 | A1* | 9/2010 | El Arab | A61B 5/363 600/518 |
| 2011/0004110 | A1* | 1/2011 | Shusterman | G16H 50/20 600/509 |
| 2011/0098775 | A1 | 4/2011 | Allavatam et al. | |
| 2011/0218950 | A1* | 9/2011 | Mirowski | G06N 3/084 706/58 |
| 2011/0270346 | A1 | 11/2011 | Frei et al. | |
| 2012/0290521 | A1* | 11/2012 | Frank | G06N 20/00 706/45 |
| 2013/0103624 | A1* | 4/2013 | Thieberger | G06N 20/00 706/12 |
| 2013/0117207 | A1* | 5/2013 | Kim | G06N 3/08 706/20 |
| 2014/0022250 | A1* | 1/2014 | Mansi | G06T 7/149 345/420 |
| 2014/0149177 | A1* | 5/2014 | Frank | G06Q 10/06 705/7.29 |
| 2014/0257122 | A1* | 9/2014 | Ong | A61B 5/0205 705/2 |
| 2015/0045684 | A1* | 2/2015 | Schie | A61B 5/726 600/509 |
| 2015/0057512 | A1* | 2/2015 | Kapoor | A61B 5/02405 600/513 |
| 2015/0065815 | A1* | 3/2015 | Najarian | G16H 40/63 600/324 |
| 2015/0106020 | A1* | 4/2015 | Chung | G16H 40/67 702/19 |
| 2015/0216432 | A1* | 8/2015 | Yang | A61B 5/7264 600/512 |
| 2015/0223759 | A1* | 8/2015 | Ong | A61B 5/7264 600/301 |
| 2016/0022162 | A1 | 1/2016 | Ong et al. | |
| 2016/0082277 | A1 | 3/2016 | Foshee et al. | |
| 2016/0278659 | A1 | 9/2016 | Kaib et al. | |
| 2016/0360980 | A1* | 12/2016 | Sinha | G16H 30/20 |
| 2017/0032221 | A1* | 2/2017 | Wu | G06F 18/2178 |
| 2017/0156614 | A1* | 6/2017 | Ibáñez Català | A61B 5/02405 |
| 2017/0319278 | A1* | 11/2017 | Trayanova | A61B 6/032 |
| 2017/0368363 | A1 | 12/2017 | Foshee et al. | |
| 2019/0082988 | A1* | 3/2019 | Datta | A61B 5/361 |
| 2019/0282823 | A1* | 9/2019 | Freeman | A61N 1/3993 |
| 2020/0155015 | A1* | 5/2020 | Ashrafi | A61B 5/7264 |

OTHER PUBLICATIONS

International Search Report issued in corresponding International Patent Application No. PCT/FR2019/050682 dated Jul. 4, 2019, with English translation.
First Office Action dated Aug. 30, 2023, from corresponding Chinese Application No. 201980023485.7.
First Search dated Aug. 30, 2023, from corresponding Chinese Application No. 201980023485.7.
Examination Report dated Mar. 21, 2024, from corresponding European Application No. 19718802.2.

* cited by examiner

COMPUTING DEVICE FOR DETECTING HEART RHYTHM DISORDERS

CROSS REFERENCE TO RELATED APPLICATIONS

This is a U.S. National Phase Application under 35 U.S.C. § 371 of International Patent Application No. PCT/FR2019/050682, filed Mar. 26, 2019, which claims priority of French Patent Application No. 1852850, filed Mar. 30, 2018. The entire contents of which are hereby incorporated by reference.

FIELD OF THE INVENTION

The invention relates to the field of computing devices for detecting heart rhythm disorders, and in particular for detecting areas of heart conducive to atrial fibrillation.

BACKGROUND

The field of detecting areas of heart conducive to atrial fibrillation comprises computing devices operating in delayed time implementing software such as the Topera and CardioInsight software, in addition to computing devices operating in real time implementing software such as the CARTO software.

The Topera software aims to reconstruct the electrical activation of the atria of the heart. Signal acquisition is carried out by means of a basket catheter (a catheter which is deployed over the entire atrium). Analysis takes place in delayed time, more than 2 minutes after the start of the acquisition. This solution is tedious since this type of catheter is difficult to install and since the contact of the electrodes is not guaranteed. The analysis time is very long, and the reconstruction does not procure high-definition maps, and may even fail in the case of complex electrical activations (which represents 70% of atrial fibrillation cases) as a result of a too simplistic reconstruction.

The CardioInsight software aims to reconstruct the electrical activity of the heart using a multi-electrode electrocardiogram measuring vest on the patient's skin. The patient wears the vest before surgery and the data are analyzed and are then accessible during surgery. Analysis takes place in delayed time (more than 15 minutes) after the start of the acquisition. This solution has the drawback of a very high computation time, which requires a time delay making it difficult to implement (more specifically, the patient must arrive several days in advance and wear the vest so that the data can be extracted before surgery), and is very expensive. Moreover, the reconstruction does not procure high-definition maps as a result of the measurements being too peripheral and distant, and fails in the case of complex electrical activations as a result of a too simplistic reconstruction.

The CARTO software edited by Biosense & Webster allows algorithms to be implemented to detect cardiac arrhythmia.

Thus, the CFAE (Complex Fractionated Atrial Electrograms) algorithm computes the number of inflection points (points where the derivative changes sign) in the signals and produces real-time color maps. The practitioner then interprets these complex maps to determine the places of interest. This algorithm is not very specific and is relatively simple.

The Ripple (Ripple Mapping) algorithm is a module of the CARTO software which allows the electrical activity of the atria to be reproduced after a first passage of a catheter. The amplitude and the propagation of the electric waves are made visible by this module. This results in maps that are extremely difficult to understand for the practitioner. Although this can work for simple cases, the analysis fails in the case of complex electrical activations since the maps are too difficult to interpret.

SUMMARY

It thus appears that no computing device for detecting heart rhythm disorders is available, allowing a practitioner to quickly and reliably detect heart rhythm disorders, including in cases of complex electrical activations.

The invention improves the situation. For this purpose, the invention proposes a device for detecting heart rhythm disorders which comprises a memory arranged to receive cardiac electrogram data and to store data defining a first classification model for detecting heart rhythm disorders and a second classification model for detecting heart rhythm disorders, the first classification model for detecting heart rhythm disorders being derived from the processing, by machine learning, of data associated with cardiac electrograms having a first duration, and the second classification model for detecting heart rhythm disorders being derived from the processing, by machine learning, of data associated with cardiac electrograms having a second duration, the first duration being less than the second duration, a classifier arranged to analyze cardiac electrogram data based on a classification model, and to return a classification value, and a driver arranged to store in the memory cardiac electrogram data received as input, on the one hand to aggregate these data according to the first duration and analyze them with the classifier on the basis of the first classification model for detecting heart rhythm disorders, and on the other hand to aggregate these data according to the second duration and analyse them with the classifier on the basis of the second classification model for detecting heart rhythm disorders, and to return alert data when the analysis by the classifier on the basis of the first classification model returns a classification value associated with a heart rhythm disorder.

This device is particularly advantageous since it procures a far more reliable and faster detection than existing devices. In various alternative embodiments, the device according to the invention can have one or more of the following features:

the second duration is an integer multiple of the first duration, and wherein the driver is arranged to apply the second classification model for detecting heart rhythm disorders such that the classification value for electrogram data having the second duration corresponds to a linear combination of the classification values obtained by cutting the electrogram data having the second duration into a plurality of sub-groups of electrogram data having the first duration and by applying the first classification model for detecting heart rhythm disorders to each of these sub-groups of electrogram data, the driver is arranged to compute a weighted average of the classification values obtained by applying the first classification model for detecting heart rhythm disorders to each of the sub-groups of electrogram data, the device according to one of the preceding claims, further comprising a machine learning engine arranged to determine the first classification model for detecting heart rhythm disorders and the second classification model for detecting heart rhythm disorders, and the learning engine is arranged to carry out a learning method selected from among supervised learning, semi-supervised learning, unsupervised learning, or a combination of two or more of these learning methods.

The invention further relates to a method for detecting heart rhythm disorders implemented by a computer comprising the following operations of:

a) receiving cardiac electrogram data, b) aggregating the data received during operation a) on the one hand according to a first duration and on the other hand according to a second duration, the first duration being less than the second duration, c) analyzing the data aggregated according to the first duration on the basis of a first classification model for detecting heart rhythm disorders, the first classification model for detecting heart rhythm disorders being derived from the processing, by machine learning, of data associated with cardiac electrograms having the first duration, and determining a first classification value, d) analyzing the data aggregated according to the second duration on the basis of a second classification model for detecting heart rhythm disorders, the second classification model for detecting heart rhythm disorders being derived from the processing, by machine learning, of data associated with cardiac electrograms having the second duration, and determining a second classification value, and e) emitting alert data when the first classification value is associated with a heart rhythm disorder.

In various alternative embodiments, the device according to the invention can have one or more of the following features:

the second duration is an integer multiple of the first duration, and the computation of the second classification value in operation d) comprises computing a linear combination of first classification values obtained by cutting the electrogram data having the second duration into a plurality of sub-groups of electrogram data having the first duration and by applying operation c) to these sub-groups of electrogram data, the linear combination in operation d) comprises computing a weighted average of the first classification values obtained by applying the first classification model for detecting heart rhythm disorders to the sub-groups of electrogram data having the first duration, the first classification model for detecting heart rhythm disorders and the second classification model for detecting heart rhythm disorders are obtained by machine learning, and the machine learning method is a learning method selected from among supervised learning, semi-supervised learning, unsupervised learning, or a combination of two or more of these learning methods.

BRIEF DESCRIPTION OF THE DRAWINGS

Other features and advantages of the invention will be better understood upon reading the following description drawn from non-limiting examples provided for illustration purposes, drawn from the drawings, in which.

DETAILED DESCRIPTION

The drawings and the description that follow essentially contain elements of a definite nature. They may therefore serve not only to assist with the understanding of the present invention, but also to contribute to the definition thereof, where appropriate.

The present description contains elements for which a claim for copyright is likely to have been made. The copyright owner has no objection to the reproduction by anyone of the present patent document or the description thereof, as it appears in the official records, but reserves all other copyright rights.

Figure 1:
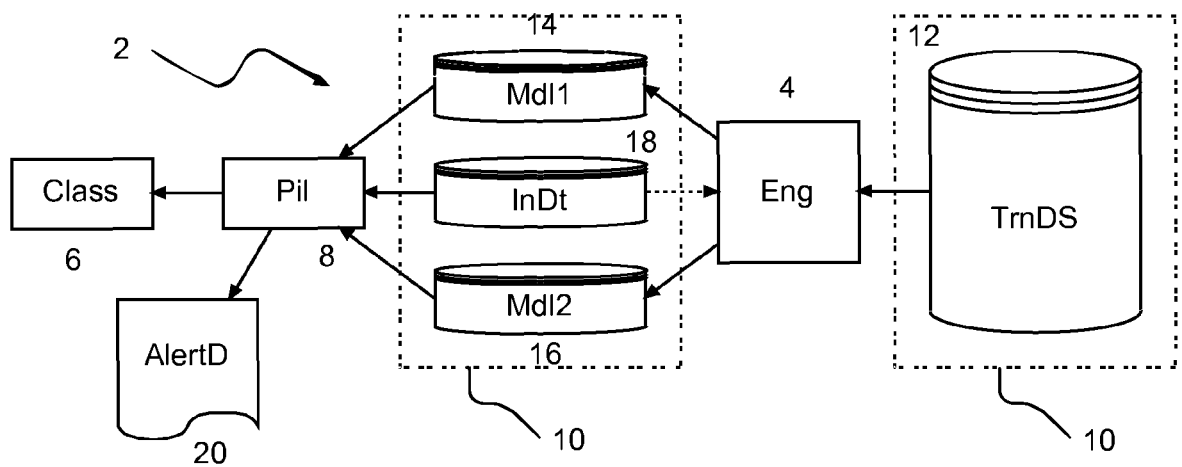
FIG. 1 shows an embodiment of a device according to the invention.

FIG. 1 shows an embodiment of a device for detecting heart rhythm disorders according to the invention.

The device 2 comprises an engine 4, a classifier 6, a driver 8 and a memory 10.

In the example described here, the device 2 is implemented on a computer which receives cardiac electrogram data as input and provides an output to a practitioner via a graphical user interface not shown. This computer is, in this case, a personal computer provided with the Windows 10 operating system, and a graphics card capable of managing one or more displays. Of course it can be made in a different manner, with a different operating system, with wireless or wired communication with the one or more displays. The term 'computer' must be interpreted in the broad sense. For example, it can be a tablet or a smartphone, an interaction terminal with a compute server, or an element on a distributed resource grid, etc.

The engine 4, the classifier 6 and the driver 8 are, in this case, programs run by the processor of the computer. Alternatively, one or more of these elements could be implemented in a different manner by means of a dedicated processor. The term 'processor' must be understood to mean any processor adapted to the data processing operations described hereafter. Such a processor can be made in any known manner, in the form of a microprocessor for a personal computer, a dedicated chip of the FPGA or SoC (System on Chip) type, a computing resource on a grid, a microcontroller, or any other form suitable for providing the computing power required to carry out the operations described hereafter. One or more of these elements can also be made in the form of specialized electronic circuits such as an ASIC. An electronic circuit-processor combination can also be considered.

The memory 10 can be any type of data storage suitable for receiving digital data: hard drive, solid state drive (SSD), flash drive of any form, random access memory, magnetic drive, cloud or local distributed storage, etc. The data computed by the device 2 can be stored in any type of memory similar to the memory 10, or therein. These data can be erased after the device has carried out its tasks, or they can be saved.

As shown in FIG. 1, the memory 10 receives a plurality of different types of data which contribute to the functioning of the device 2. Thus, the engine 4 accesses training data 12 to compute a first classification model for detecting heart rhythm disorders 14 and a second for detecting heart rhythm disorders 16. These data are then used to classify input data 18.

In the example described here, the engine 4 is a supervised machine learning engine. Thus, the training data 12 comprise cardiac electrograms which have been labelled to indicate whether or not they are associated with a sought cardiac disorder. In the example described here, the cardiac disorder targeted concerns atrial fibrillation. In other embodiments, it can be one or more other cardiac disorders.

Also alternatively, the engine 4 can use another machine learning engine, for example a semi-supervised or unsupervised machine learning engine. The dotted arrow between the input data 18 and the engine 4 represent the capacity of the latter to operate in semi-supervised or unsupervised mode. The engine 4 can also implement a combination of supervised, semi-supervised and/or unsupervised machine learning methods. In the example described here, the engine 4 mainly uses a data clustering algorithm.

Alternatively, the engine 4 can implement a regression algorithm, an instance-based algorithm, a regularization algorithm, a decision tree, a Bayesian algorithm, a neural network, a deep learning algorithm, or a combination thereof.

Alternatively, the engine 4 can be omitted, and the device 2 can operate based on predefined models for detecting heart rhythm disorders.

In the embodiment described here, the input data represent cardiac electrograms, i.e. the electric signals derived from the cardiac activity. To process them, these electrograms are cut into sequences of a chosen duration. In a preferred manner, this duration corresponds to the parameters of the model used for detecting heart rhythm disorders. This means that, in general, the duration with which the electrogram data are cut for determining the model for the engine 4 is the same as the duration of the electrogram data used by the device 2 during the operational functioning thereof.

Thus, the driver 8 receives the input data and cuts them according to the duration associated with the model with which the classification is sought, then the classifier 6 is called with the model and the cut data.

The Applicant has discovered that the detection was more effective when two models are used. For this purpose, the first model for detecting heart rhythm disorders is established using a first duration for the electrogram data, in the example described here, of 5 seconds, whereas the second model for detecting heart rhythm disorders is established using a second duration, which is an integer multiple of the first duration. In the example described here, the integer multiple is equal to 5. Alternatively, it can vary between 2 and 10.

In the example described here, these two models use the smallest of two estimators computed from the electrogram data. The purpose of these estimators is to qualify the cycle duration associated with the electrogram data. For this purpose, the electrogram data are stored in a vector, each element whereof corresponds to a sample of the signal represented by the electrogram data. Then, an autocorrelation parameter T is used to define two vectors of size T: a first vector comprising the first T samples of the electrogram data vector, and a second vector comprising the last T samples of the electrogram data vector.

In the example described here, the first estimator is computed by measuring a normalized autocorrelation by determining the scalar product of the first vector and of the second vector, divided by the product of the Euclidean norms of the first vector and of the second vector. By varying T, a maximum value and a minimum value of the first estimator are determined, then the value retained for the first estimator is chosen to be that for which the value of T is the smallest and such that the first estimator computed with this T value is greater than the difference between the maximum value of the first estimator subtracted from 0.3 times the difference between the maximum value and the minimum value of the first estimator. Alternatively, the first estimator can be determined differently, for example by changing the coefficient of 0.3, or by searching for a T value that optimizes the estimator, in an empiric, or exhaustive manner or by machine learning.

In the example described here, the second estimator is computed by computing, for each T value, the Euclidean norm squared of the difference between the first vector and the second vector, divided by the product of the sample having the highest absolute value in the first vector and the sample having the highest absolute value in the second vector. As for the first estimator, a maximum value and a minimum value of the second estimator are determined, then the value retained for the second estimator is chosen to be that for which the value of T is the smallest and such that the second estimator computed with this T value is greater than the difference between the minimum value of the second estimator added to 0.2 times the difference between the maximum value and the minimum value of the second estimator. Alternatively, the first estimator can be determined differently, for example by changing the coefficient of 0.3, or by searching for a T value that optimizes the estimator, in an empiric, or exhaustive manner or by machine learning.

Also alternatively, the first model and the second model can be based on other features, in addition to or in replacement of the first and second estimators.

The combination of these two models is particularly advantageous since the first model is extremely fast to implement since the first duration is short, whereas the second model is extremely precise although the second duration is much longer.

It should be noted that the cardiac electrograms are obtained by moving an electrode inside the heart in the areas of interest. The speed of movement of the electrode is thus crucial for the detection, however it must not be too slow in order to limit surgical risks. This speed of movement of the electrode inevitably influences the measurement precision. More specifically, as the electrode is progressively moved from a first area to a second area, the measurements taken are decreasingly associated with the first area, and increasingly associated with the second area.

Within the scope of the invention, this can make the second model for detecting heart rhythm disorders less efficient as a result of the longer duration of the second duration. Thus, although the first model is less precise, it procures a primary detection of the areas of interest in which a practitioner must spend more time so that the second model can indicate, with certainty, whether these areas are relevant. It should be noted that this advantage remains valid whether the device according to the invention is used in real time during a procedure or it is in delayed mode, in order to limit false negatives, i.e. areas which should have been detected as relevant, but for which the practitioner moved on "too quickly".

Conventionally, when the classifier 6 applies the first model for detecting heart rhythm disorders or the second model for detecting heart rhythm disorders to cardiac electrogram data, it returns a value at the output. This value represents a probability of whether the electrogram data in question are considered to be indicative of a detection of a heart rhythm disorder.

Advantageously, when the driver 8 applies the first model for detecting heart rhythm disorders to cardiac electrogram data and when the response value exceeds a chosen detection threshold (for example 70%), alert data 20 are emitted. Nonetheless, it is only when the second model for detecting heart rhythm disorders returns a response value that exceeds a second chosen threshold (for example 80%) that an area from which the cardiac electrogram data were derived is considered to be relevant. Thus, the alert data 20 allow to indicate that an area is of interest, and calls for a more in-depth analysis in order for the second model to be optimally applied.

Figure 2:
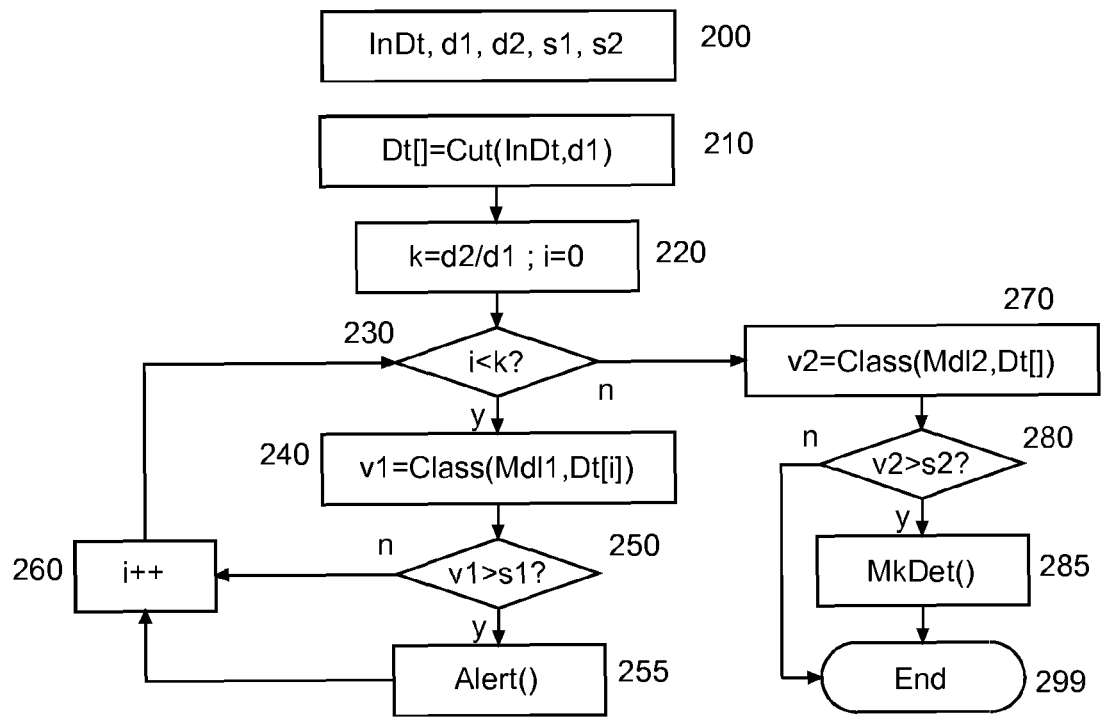
FIG. 2 shows an exemplary implementation of a function by the device in FIG. 1.

FIG. 2 shows one example implementation of a detection function by the driver 8.

This function begins with an operation 200 wherein the input data are received, in addition to the execution parameters such as the first duration d1 and the second duration d2, as well as the detection thresholds s1 for the first model and s2 for the second model.

Conventionally, the input data are received in packets. FIG. 2 shows the processing of a packet, the function being repeated for each new packet. To simplify this presentation, the example described here concerns the case whereby a data packet corresponds to the second duration. In the case whereby the packets are larger or smaller than the second duration, the function in FIG. 2 can be easily adapted to take missing or excess data into consideration.

Then, in an operation 210, the data are cut according to the first duration, then an index i is set to 0 and the integer multiple corresponding to the division of the second duration by the first duration is computed in an operation 220.

A loop is thus launched to apply the first model with each piece of the input data having the first duration, and the second model to the input data as a whole.

For this purpose, a loop exit test checks in an operation whether the index i is strictly less than the multiple k in an operation 230. When this is the case, the first model is applied to the input data block having the index i in an operation 240, and the resulting value v1 is compared with the threshold s1 in an operation 250. If the value v1 exceeds the threshold s1, the alert data are emitted in an operation 255. Conversely, or after operation 255, the index i is incremented in an operation 260 and the loop is resumed with the test in operation 230. In the example described here, the threshold value s1 can be set to 0.5. Alternatively, it can be set differently and/or be optimized.

When all of the data blocks have been browsed, an operation 270 applies the second model with all of the blocks, then the resulting value v2 is compared with the threshold s2 in an operation 280. If the value v2 exceeds the threshold s2, the detection data are emitted in an operation 285. Conversely, or after operation 285, the function ends in an operation 299. In the example described here, the threshold value s2 can be set to 0.7. Alternatively, it can be set differently and/or be optimized.

It should be noted that the classification of operation 270 can be carried out by applying a model in its own right, or even by carrying out operations based on the values derived from the application of the first model. Thus, the value v2 can be a linear combination of the values v1 computed in the loop, for example with a weighting that is all the greater given that the values v1 are associated with a high index i. More specifically, the lower the index i, the more the corresponding data are temporally distant from the detection time, and the greater the risk of the electrode being far from the area concerned.

Alternatively, other types of functions can be implemented, such as a thresholded, arithmetic mean, or any combination based on the values v1.

Also alternatively, a so-called reference catheter can be placed in an area of the heart that is known to be healthy, and the electrogram data derived therefrom can be processed to determine the first estimator and the second estimator, as described hereinabove, in order to derive the lowest estimator value. This value can be compared with the value determined in a similar manner for the current electrogram data, and a similar alert to that in operation 255 can be triggered if a difference of more than 150 ms is determined between these values, or if the current electrogram data give a value of less than 150 ms.

The invention claimed is:

1. A device for detecting heart rhythm disorders, wherein the device comprises:
   a memory storing data defining a first classification model for detecting heart rhythm disorders and a second classification model for detecting heart rhythm disorders, the first classification model for detecting heart rhythm disorders being derived from a first processing, by machine learning, of data associated with cardiac electrograms having a first duration, and the second classification model for detecting heart rhythm disorders being derived from a second processing, by machine learning, of data associated with cardiac electrograms having a second duration, the first duration being less than the second duration;
   wherein the device has stored thereon:
     a classifier program including instructions for analyzing cardiac electrogram data based on the first and second classification models, and for returning a classification value; and
     a driver program including instructions for:
       storing in the memory cardiac electrogram data received as input,
       aggregating the received cardiac electrogram data according to the first and second durations,
       analyzing the data aggregated according to the first and second durations with the classifier program on the basis of the first and second classification models respectively, and
       returning alert data when the analysis by the classifier program on the basis of the first classification model returns a classification value associated with a heart rhythm disorder;
   wherein the device further comprises at least one processor configured for executing the classifier program and the driver program;
   wherein the second duration is an integer multiple of the first duration, and wherein the driver program further includes instructions for applying the second classification model for detecting heart rhythm disorders such that the classification value for electrogram data having the second duration corresponds to a linear combination of the classification values obtained by cutting the electrogram data having the second duration into a plurality of sub-groups of electrogram data having the first duration and by applying the first classification model for detecting heart rhythm disorders to each of these sub-groups of electrogram data; and
   wherein the driver program further includes instructions for computing a weighted average of the classification values obtained by applying the first classification model for detecting heart rhythm disorders to each of the sub-groups of electrogram data.

2. The device according to claim 1, wherein the device has stored thereon a machine learning engine program including instructions for determining the first classification model for detecting heart rhythm disorders and the second classification model for detecting heart rhythm disorders, and wherein the at least one processor is further configured for executing the machine learning engine program.

3. The device according to claim 2, wherein the machine learning engine program includes instructions for carrying out a learning method selected from among supervised learning, semi-supervised learning, unsupervised learning, or a combination of two or more of these learning methods.

4. A method for detecting heart rhythm disorders implemented by a computer comprising the following operations of:
  a) receiving cardiac electrogram data,
  b) aggregating the data received according to a first duration and a second duration, the first duration being less than the second duration,
  c) analyzing the data aggregated according to the first duration with a classifier program on the basis of a first classification model for detecting heart rhythm disorders, the first classification model for detecting heart rhythm disorders being derived from a first processing, by machine learning, of data associated with cardiac electrograms having the first duration, and returning a first classification value,
  d) analyzing the data aggregated according to the second duration with a classifier program on the basis of a second classification model for detecting heart rhythm disorders, the second classification model for detecting heart rhythm disorders being derived from a second processing, by machine learning, of data associated with cardiac electrograms having the second duration, and returning a second classification value, and
  e) emitting alert data when the first classification value is associated with a heart rhythm disorder;
  wherein the second duration is an integer multiple of the first duration, and the computation of the second classification value in operation d) comprises computing a linear combination of first classification values obtained by cutting the electrogram data having the second duration into a plurality of sub-groups of electrogram data having the first duration and by applying operation c) into these sub-groups of electrogram data; and
  wherein the linear combination in operation d) comprises computing a weighted average of the first classification values obtained by applying the first classification model for detecting heart rhythm disorders to the sub-groups of electrogram data having the first duration.

5. The method according to claim 4, wherein, the first classification model for detecting heart rhythm disorders and the second classification model for detecting heart rhythm disorders are obtained by machine learning.

6. The method according to claim 5, wherein the machine learning method is a learning method selected from among supervised learning, semi-supervised learning, unsupervised learning, or a combination of two or more of these learning methods.

* * * * *